United States Patent [19]

Georgiev et al.

[11] Patent Number: 4,557,865
[45] Date of Patent: Dec. 10, 1985

[54] SUBSTITUTED 4-AZATRICYCLO[4.3.1.1$^{3,8}$]UNDECANE COMPOUNDS

[75] Inventors: Vassil S. Georgiev, Rochester; Clyde R. Kinsolving, Fairport, both of N.Y.

[73] Assignee: Pennwalt Corporation, Philadelphia, Pa.

[21] Appl. No.: 607,378

[22] Filed: May 7, 1984

[51] Int. Cl.$^4$ .......................................... C07D 223/14
[52] U.S. Cl. ...................... 260/239.3 T; 260/239 B; 260/239 BC
[58] Field of Search ................ 260/239.3 T, 239 B, 260/239 BC

[56] References Cited

U.S. PATENT DOCUMENTS 3,560,481 2/1971 Berzin ............................. 260/239 B
3,951,950 4/1976 Narayan et al. ................ 260/239 B

OTHER PUBLICATIONS

Korsloot et al., J. Med. Chem., vol. 14, pp. 411–415 (1971).
Vernier et al., "Toxicol. Appl. Pharm" vol. 15, pp. 642–655 (1969).
Korsloot et al., "Chem. Abstracts" vol. 70, Item 114987(c) (1969), [Abstracting Rec. Trav. Chem. Pays–Bays, vol. 84, pp. 447–448 (1969)].
Korsloot et al., "Tetrahedron Letters" (Pergamon) (1969), vol. 40, pp. 3517–3520.
Tonnis et al., "J. Org. Chem." vol. 39, No. 6 (1974), pp. 5766–5770.
Olivero–Desherches, "Synthesis" (1974), pp. 812–813.
Narayanan et al., "Chem. Abstracts" vol. 72, Item 90334a (1970), Abstracting German Offen 1,941,245 (Feb. 26, 1970).

Primary Examiner—Robert T. Bond

[57] ABSTRACT

5-Substituted and/or N-Substituted 4-azatriciclo [4.3.1.1$^{3,8}$]undecane and 4-azatriciclo[4.3.1.1$^{3,8}$]undecan-5-one compounds are prepared.

16 Claims, No Drawings

SUBSTITUTED 4-AZATRICYCLO[4.3.1.1³,⁸]UNDECANE COMPOUNDS

BACKGROUND OF THE INVENTION

This invention relates generally to substituted 4-azatricyclo(4.3.1.1$^{3,8}$)undecane compounds and more specifically to certain 5-substituted and/or N-substituted derivatives thereof.

A number of nitrogen-containing adamantane derivatives such as amantadiene (1) are known for their antiviral activity.

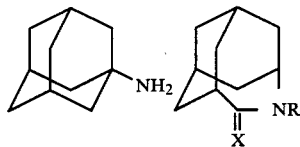

1

2 R = H, X = O
3 R = H, X = H$_2$

The introduction of a nitrogen into the lipophilic adamantane moiety to form analogs of structures such as the 4-azatricyclo[4.3.1.1$^{3,8}$]undecan-5-one (2) and its 5-dihydro analog (3) has also provided compounds that exerted either antiviral antiarrhythmic, anti-inflammatory or cardiovascular activities.

We have now found a new series of substituted 4-azatricyclo[4.3.1.1$^{3,8}$]undecane and 4-azatricyclo[4.3.1.1$^{3,8}$]undecan-5-one derivatives.

SUMMARY OF THE INVENTION

In accordance with this invention there are provided substituted 4-azatricyclo[4.3.1.1$^{3,8}$]undecane compounds having the general formula:

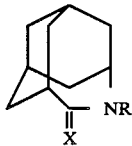

Where X is selected from, H$_2$, O, S and N—NHR', where R' is alkoxycarbonyl; and Where R is selected from H, H.HI, benzoyl, substituted benzoyl, cinnamoyl, substituted cinnamoyl, propargyl, phenylpropenyl, substituted phenylpropenyl, 3-[3'(4"-methylene-4"-azatricyc-lo[4.3.1.1$^{3,8}$]undecane)azobenzene]methylene, and 4-[4'-(4"'methylene-4"-azatricyclo[4.3.1.1$^{3,8}$]undecane)azobenzene]methylene;
and When R is H, X≠H$_2$ or O.

DETAILED DESCRIPTION

The compounds of the invention can be prepared from compounds 2 and 3 starting with 2-adamantanone oxime.

Beckman rearrangement of 2-adamantanone oxime provides 4-azatricyclo[4.3.1.1$^{3,8}$]undecane-5-one (2) and catalytic reduction of 2 furnishes the 4-azatricyclo[4.3.1.1$^{3,8}$]undecane (3). Compound 3 is then N-acylated using appropriate acyl halides to provide the benzoyl, cinnamoyl, and phenylpropenyl derivatives (for example compounds 4a to 4f in Table I below). The benzoyl, cinnamoyl and the phenyl ring of the phenylpropenyl can be optionally substituted with alkyl (preferable 1 to 8 carbon atoms), haloalkyl, alkoxy, nitro, amino, hydroxyl, and carboxyl groups. Lithium aluminum hydride reduction of the N-m-(or-p-)nitrobenzoyl analogs (compounds 4a and 4b) is used to prepare the corresponding azobenzenes (for example compounds 4g and 4h in Table I below).

N-alkylation of compound 2 yields the propargyl derivatives (for example compound 5a in Table II below). The 4-azatricyclo[4.3.1.1$^{3,8}$]undecane-5-thione (compound 5c in Table II) and its methylthio analogue, 5-methylthio-4-azatricyclo[4.3.1.1$^{3,8}$]undec-4-ene hydroiodide (6)

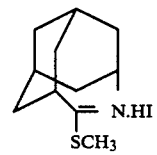

6 are obtained by treatment of compound 2 with phosphorous pentasulfide and subsequent reaction with methyl iodide. Reaction of compound 6 with alkyl carbazates gives the corresponding alkoxycarbonyl hydrazonyl derivatives (for example compound 5b in Table II).

EXAMPLE 1

4-(p-Nitrobenzoyl)-4-azatricyclo[4.3.1.1.$^{3,8}$]undecane (4b) was prepared as follows:

A. Preparation of 4-Azatricyclo[4.3.1.1.$^{3,8}$]undecan-5-one (2)

To a suspension of 3 grams (18 mmol) of 2-adamantanone oxime in 36 ml of 20% aqueous sodium hydroxide were added 5 grams (28 mmol) of benzenesulfonyl chloride with vigorous stirring at a temperature of 20°–30° C. The temperature was maintained below 30° C. until the exothermic reaction ceased, then raised to 55° C. and held there for 2 hours. The reaction mixture was worked up leaving 2 grams of 4-azatricyclo[4.3.1.1$^{3,8}$]undecan-5-one as white crystals melting at 306°–308° C. (recrystallized from hexane).

Anal. Calcd. for C$_{10}$H$_{15}$NO: C,72.69; H,9.15; N,8.47. Found: C,72.29; H,9.26; N,8.34.

B. Preparation of 4-Azatricyclo[4.3.1.1$^{3,8}$]undecane (3)

4-Azatricyclo[4.3.1.1$^{3,8}$]undecan-5-one, 2.45 grams (14 mmol), was added to a suspension of lithium aluminum hydride (2.12 grams, 56 mmol) in 200 ml of anhydrous ether. The mixture was refluxed for 6 hours then worked up to give compound 3 as a white solid material recrystallized from hexane (melting point 290° C.).

C. Preparation of 4-(p-Nitrobenzoyl)-4-azatricyclo[4.3.1.1$^{3,8}$]undecane (4b)

A mixture of 4-azatricyclo[4.3.1.1$^{3,8}$]undecane (0.75 gram, 5 mmol) from Step B, and p-nitrobenzoyl chloride (0.93 gram, 5 mmol) in 40 ml anhydrous ethanol was refluxed for 4.5 hours. Following workup and recrystallization from isopropanol, 1.25 gram of compound 4b were obtained as white crystals (melting point 150° C.).

Anal. Calcd. for $C_{17}H_{20}N_2O_3$: C,67.98; H,6.71; N,9.32. Found: C,67.53; H,6.95; N,9.17.

Compounds 4a and 4c-e were prepared by procedures similar to those described for compound 4b.

EXAMPLE 2

Preparation of 4-(3-Phenylpropen-2-yl)-4-azatricyclo[4.3.1.1$^{3,8}$]undecane Hydrochloride (4f)

A reaction mixture containing 4-azatricyclo[4.3.1.1.$^{3,}$$_{8}$]undecane (0.75 gram, 5 mmol) and cinnamyl chloride (0.76 gram, 5 mmol) in 40 ml anhydrous ethanol was refluxed for 8 hours. After workup, 1.05 gram of compound 4f was obtained as white crystals melting at 273° C. (recrystallized from isopropyl alcohol).

Anal. Calcd. for $C_{19}H_{26}ClN$: C,75.12; H,8.59; Cl,11.68; N,4.61. Found: C,75.02; H,8.84; Cl,11.56; N,4.62.

This compound was found to have activity against influenza A and type 2 Herpesvirus in vitro.

EXAMPLE 3

Preparation of 4,4'-Bis(4"-methylene-4"-azatricyclo[4.3.1.1$^{3,8}$]undecane)azobenzene (4h)

4-(p-Nitrobenzoyl)-4-azatricyclo[4.3.1.1.$^{3,8}$]undecane (0.37 gram, 1.2 mmol) was added to a suspension of lithium aluminum hydride (0.37 gram, 9.8 mmol) in 100 ml of diethyl ether, and the reaction mixture was refluxed for 7.5 hours. After workup, 54 mg of derivative 4h were obtained as white crystals. Melting point 196°-198° C. (recrystallized from isopropanol).

Anal. Calcd. for $C_{34}H_{44}N_4$: C,80.27; H,8.72; N,11.01. Found: C,79.76; H,8.68; N,10.91.

The synthesis of the azobenzene analog 4g was similar to that described for compound 4h. The 4g analog was found to be active against type 2 Herpesvirus in vitro.

EXAMPLE 4

Preparation of 4-Propargyl-4-azatricyclo[4.3.1.1$^{3,8}$]undecan-5-one (5a)

A solution of potassium hydroxide (0.56 gram, 10 mmol) in 3 ml of absolute methanol was added to 4-azatricyclo[4.3.1.1$^{3,8}$]undecan-5one (1.65 gram, 10 mmol) and the solvent was slowly removed under reduced pressure with the internal temperature not exceeding 25° C. When solid began to separate, anhydrous toluene was added and the solvent removal continued (a total of 30 ml of toluene were removed), then the temperature was raised to 90° C. (with the distillation continuing at atmospheric pressure—a total of 10 ml of toluene were distilled). The reaction mixture was cooled to 40° C. and propargyl bromide (0.9 ml, 10 mmol) was added dropwise. The temperature was raised to 65° C. and the mixture stirred for 4 hours. The solid precipitate was filtered off, and the filtrate was evaporated to yield 1.82 gram of compound 5a. Melting point 168°-170° C. (recrystallized from a petr. ether-ethanol 10:1 mixture by volume).

Anal. Calcd. for $C_{13}H_{17}NO$: C,76.81; H,8.42; N,6.89. Found: C,76.68; H,8.82; N, 6.85.

EXAMPLE 5

Preparation of 4-Azatricyclo[4.3.1.1$^{3,8}$]undecane-5-thione (5c)

4-Azatricyclo[4.3.1.1$^{3,8}$]undecan-5-one (3 grams, 18 mmol) and phosphorus pentasulfide (4.65 grams, 21 mmol) were dissolved in 100 ml of pyridine and the solution was refluxed for 45 minutes. The mixture was poured into 150 ml of ice-cold saturated sodium chloride solution with continuous stirring. The resulting precipitate was filtered, washed with water and then dissolved in methylene chloride. The organic solution was filtered through activated alumina and then evaporated to yield 1.72 gram of the 5-thione analog 5c. Melting point 184°-185° C. (recrystallized from absolute ethanol).

Anal. Calcd. for $C_{10}H_{15}NS$: C,66.25; H,8.34; N,7.73; S,17.68. Found: C,66.31; H,8.46; N,7.74; S,18.00.

EXAMPLE 6

A. Preparation of 5-Methylthio-4-azatricyclo[4.3.1.1$^{3,8}$]undec-4-ene Hydroiodide (6)

A mixture of the 5-thione derivative 5c (1.45 gram, 8 mmol) and methyl iodide (1.21 gram, 8.5 mmol) in 100 ml methanol was refluxed for 6 hours. The solvent was evaporated to dryness leaving the hydroiodide salt 6 (2 grams) as a white solid. Melting point 235°-238° C. (recrystallized from absolute ethanol).

Anal. Calcd. for $C_{11}H_{18}INS$: C,40.87; H,5.61; I,39.26; N,4.33; S,9.92. Found: C,40.86; H,5.76; I,38.95; N,4.32; S,9.86.

B. Preparation of 5-(Ethoxycarbonyl)hydrazonyl]-4-azatricyclo[4.3.1.1$^{3,}$$_{8}$]undecane Hydroiodide (5b)

A mixture of the hydroiodide salt 6 (0.5 gram, 2.56 mmol) and ethyl carbazate (0.31 gram, 3 mmol) in 50 ml of toluene was refluxed for 6 hours. The resulting precipitate was filtered off and recrystallized from ethyl acetate leaving 0.24 gram of compound 5b as a white crystalline material melting at 185°-187° C.

Anal. Calcd. for $C_{13}H_{22}IN_3O_2$: C,41.17; H,5.85; I,33.46; N,11.08. Found: C,40.81; H,5.85; I,33.23; N,11.14.

TABLE I

N—Substituted 4-Azatricyclo[4.3.1.1$^{3,8}$]undecane Derivatives

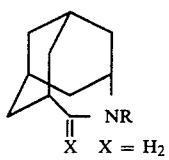

X  X = H$_2$

4

| No | R | Mp, °C. | recryst solvent | formula |
|---|---|---|---|---|
| 4a | COC$_6$H$_4$NO$_2$—3 | 122 | isopropanol | C$_{17}$H$_{20}$N$_2$O$_3$ |
| 4b | COC$_6$H$_4$NO$_2$—4 | 150 | isopropanol | C$_{17}$H$_{20}$N$_2$O$_3$ |
| 4c | COCH=CHC$_6$H$_4$OCH$_3$—4 | 170–172 | abs. ethanol | C$_{20}$H$_{25}$NO$_2$ |
| 4d | COCH=CHC$_6$H$_4$NO$_2$—4 | 290–293 | abs. ethanol | C$_{19}$H$_{22}$N$_2$O$_3$ |
| 4e | COCH=CHC$_6$H$_4$CF$_3$—3 | 95–100 | petr. ether | C$_{20}$H$_{22}$F$_3$NO |
| 4f | CH$_2$CH=CHC$_6$H$_5$.HCl | 273 | isopropanol | C$_{19}$H$_{26}$ClN |
| 4g | 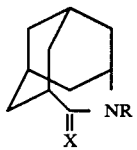 | 127 | abs. ethanol | C$_{34}$H$_{44}$N$_4$ |
| 4h | | 196–198 | isopropanol | C$_{34}$H$_{44}$N$_4$ |

TABLE II

5-Substituted 4-Azatricyclo[4.3.1.1$^{3,8}$]undecane Derivatives

5

| No. | R | X | Mp, °C. | recryst solvent | formula |
|---|---|---|---|---|---|
| 5a | CH$_2$C≡CH | O | 168–170 | ether-ethanol | C$_{13}$H$_{17}$NO |
| 5b | H.HI | NNHCO$_2$C$_2$H$_5$ | 185–187 | ethyl acetate | C$_{13}$H$_{22}$IN$_3$O$_2$ |
| 5c | H | S | 184–185 | abs. ethanol | C$_{10}$H$_{15}$NS |
| | | 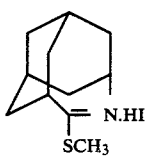 | 235–238 | abs. ethanol | C$_{11}$H$_{18}$INS |

6

The compounds of the invention are useful for example as antiviral agents and such activity was demonstrated by the in vitro testing of the 4-(3-phenylpropen-2-yl)-4-azatricyclo[4.3.1.1$^{3,8}$]undecane hydrochloride and 4,4′-bis(4″-methylene-4″-azatricyclo[4.3.1.1$^{3,8}$]undecane)azobenzene compounds.

We claim:

1. A compound having the formula:

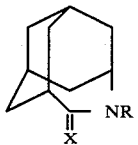

Where X is selected from $H_2$, O, S, and N—NHR', where R' is alkoxycarbonyl, and Where R is selected from H, H HI, benzoyl, cinnamoyl, propargyl, phenylpropenyl, and 3-[3'-(4"-methylene-4"-azatricyclo[4.3.1.1$^{3,8}$]undecane)azobenzene]methylene, and 4-[4'-(4"-methylene-4"-azatricyclo[4.3.1.1$^{3,8}$]undecane)azobenzene]methylene, wherein the benzoyl, cinnamoyl and the phenyl ring of the phenylpropenyl can be substituted with one or more groups selected from alkyl of 1 to 8 carbon atoms, haloalkyl, alkoxy, nitro, amino, hydroxyl, and carboxyl, and when R is H, X$\neq$H$_2$ or O and when R is benzoyl, X$\neq$O.

2. A compound according to claim 1 wherein X is $H_2$.

3. A compound according to claim 2 wherein R is benzoyl.

4. A compound according to claim 2 wherein R is $COC_6H_4NO_2$-3.

5. A compound according to claim 2 wherein R is $COC_6H_4NO_2$-4.

6. A compound according to claim 2 wherein R is cinnamoyl.

7. A compound according to claim 2 wherein R is $COCH=CHC_6H_4OCH_3$-4.

8. A compound according to claim 2 wherein R is $COCH=CHC_6H_4NO_2$-4.

9. A compound according to claim 2 wherein R is $COCH=CHC_6H_4CF_3$-3.

10. A compound according to claim 2 wherein R is phenylpropenyl.

11. A compound according to claim 10 wherein R is $CH_2CH=CHC_6H_5 \cdot HCl$.

12. A compound according to claim 1 wherein the compound is 4-propargyl-4-azatricyclo[4.3.1.1$^{3,8}$]undecan-5-one.

13. A compound according to claim 1 wherein the compound is 5-[(ethoxycarbonyl)hydrazonyl]-4-azatricyclo[4.3.1.1$^{3,8}$]undecane hydroiodide.

14. A compound according to claim 1 wherein the compound is 4-azatricyclo[4.3.1.1$^{3,8}$]undecane-5-thione.

15. A compound according to claim 2 wherein R is 4-[4'-(4"-methylene-4"-azatricyclo[4.3.1.1$^{3,8}$]undecane)azobenzene]methylene.

16. A compound according to claim 2 wherein R is 3-[3'-(4"-methylene-4"-azatricyclo[4.3.1.1$^{3,8}$]undecane)azobenzene]methylene.

* * * * *